US006914279B2

(12) United States Patent
Lu et al.

(10) Patent No.: US 6,914,279 B2
(45) Date of Patent: Jul. 5, 2005

(54) MULTIFUNCTIONAL BIOSENSOR BASED ON ZNO NANOSTRUCTURES

(75) Inventors: Yicheng Lu, East Brunswick, NJ (US); Zheng Zhang, Bellemead, NJ (US); Nuri William Emanetoglu, Woodbury, NJ (US); Masayori Inouye, New Brunswick, NJ (US); Oleg Mirochnitchenko, East Brunswick, NJ (US)

(73) Assignees: Rutgers, The State University of New Jersey, New Brunswick, NJ (US); University of Medicine and Dentistry of NJ, New Brunswick, NJ (US)

( * ) Notice: Subject to any disclaimer, the term of this patent is extended or adjusted under 35 U.S.C. 154(b) by 68 days.

(21) Appl. No.: 10/456,050

(22) Filed: Jun. 6, 2003

(65) Prior Publication Data

US 2005/0116263 A1 Jun. 2, 2005

Related U.S. Application Data

(60) Provisional application No. 60/385,884, filed on Jun. 6, 2002.

(51) Int. Cl.[7] .............................................. H01L 29/82
(52) U.S. Cl. ...................... 257/252; 257/253; 257/414; 310/313 A; 310/313 R
(58) Field of Search ................................ 257/252, 253, 257/414; 310/313 A, 313 R (56) References Cited

U.S. PATENT DOCUMENTS

| | | | | |
|---|---|---|---|---|
| 5,140,393 A | * | 8/1992 | Hijikihigawa et al. | 257/252 |
| 5,440,189 A | * | 8/1995 | Nakahata et al. | 310/313 R |
| 6,626,026 B2 | * | 9/2003 | Banda et al. | 73/24.01 |
| 6,673,644 B2 | * | 1/2004 | Gole et al. | 438/49 |

FOREIGN PATENT DOCUMENTS

| WO | WO99/35312 | 7/1999 |
|---|---|---|
| WO | WO99/54718 | 10/1999 |
| WO | WO02/07309 A2 | 1/2002 |
| WO | WO02/17362 A2 | 2/2002 |

OTHER PUBLICATIONS

Emanetoglu et al. $Mg_xZn_{1-x}O$: A New Piezoelectric Material, IEEE Ultrasonics Symposium, pp. 253–256, 2001.
Kalantar–Zadeh et al. A Novel Love Mode SAW Sensor with ZnO layer Operating in Gas and Liquid Media, IEEE Ultrasonics Symposium, pp. 353–356, 2001.
Yuan et al. Current—Voltage Properties of Piezoelectric Thin Film ZnO in a Micromechanical Force sensor, IEEE Ultrasonics Symposium, pp. 593–596, 1998.

(Continued)

Primary Examiner—David Nelms
Assistant Examiner—Dao H. Nguyen
(74) Attorney, Agent, or Firm—Hoffmann & Baron, LLP (57) ABSTRACT

The present invention provides the multifunctional biological and biochemical sensor technology based on ZnO nanostructures. The ZnO nanotips serve as strong DNA or protein molecule binding sites to enhance the immobilization. Patterned ZnO nanotips are used to provide conductivity-based biosensors. Patterned ZnO nanotips are also used as the gate for field-effect transistor (FET) type sensors. Patterned ZnO nanotips are integrated with SAW or BAW based biosensors. These ZnO nanotip based devices operate in multimodal operation combining electrical, acoustic and optical sensing mechanisms. The multifunctional biosensors can be arrayed and combined into one biochip, which will enhance the sensitivity and accuracy of biological and biochemical detection due to strong immobilization and multimodal operation capability. Such biological and biochemical sensor technology are useful in detection of RNA-DNA, DNA-DNA, protein-protein, protein-DNA and protein-small molecules interaction. It can be further applied for drug discovery, and for environmental monitoring and protection.

58 Claims, 5 Drawing Sheets

OTHER PUBLICATIONS

G. Marrazza, et al., "Disposable DNA Electrochemical Sensor for Hybridization Detection", *Elsevier Science B. V.*, Biosensors & Bioelectronics 14 (1999), pp. 43–51.

Sara Tombelli, et al., "Coupling of a DNA Piezoelectric Biosensor and Polymerase Chain Reaction to Detect Apolipoprotein E Polymorphisms", *Elsevier Science S.A.*, Biosensors & Bioelectronics 15 (2000), pp. 363–370.

T. Andrew Taton, et al., "Scanometric DNA Array Detection with Nanoparticle Probes", *Science*, vol. 289, pp. 1757–1760.

Linda A. Chrisey, et al., "Covalent Attachment of Synthetic DNA to Self–Assembled Monolayer Films", *Nucleic Acids Research*, vol. 24, No. 15, pp. 3031–3039.

Sangita Phadtare, et al., "Cold–Shock Response and Cold–Shock Proteins", *Elsevier Science Ltd.*, Current Opinion in Microbiology 1999, vol. 2, pp. 175–180.

M.O. Nicoletto, et al., "BRCA–1 and BRCA–2 Mutations as Prognostic Factors in Clinical Practice and Genetic Counselling", *Cancer Treatment Reviews*, vol. 27, pp. 295–304.

Dan Tong, et al., "BRCAI Gene Mutations in Sporadic Ovarian Carcinomas: Detection by PCR and Reverse Allele–specific Oligonucleotide Hybridization", *Clinical Chemistry*, 45:7 (1999) pp. 976–981.

N. Barle, et al., Covalent Bound Sensing Layers on Surface Acoustic Wave (SAW), *Elsevier Science B.V.*, Biosensors & Bioelectronics 16 (2001), pp. 979–987.

T. Wessa, et al., "New Immobilization Method for SAW–biosensors: Covalent Attachment of Antibodies via CNBr", *Elsevier Science S.A.*, Biosensors & Bioelectronics 14 (1999) pp. 93–98.

Atsushi Miyawaki, et al., "Fluorescent Indicators for $Ca^{2+}$ Based on Green Fluorescent Proteins and Calmodulin", *Nature*, vol. 388, pp. 882–887.

Yi Cui, et al., "Nanowire Nanosensors for Highly Sensitive and Selective Detection of Biological and Chemical Species", *Science*, vol. 293, Aug. 2001, pp. 1289–1292.

Victor H. Perez–Luna, et al., "Fluorescence Biosensing Strategy Based on Energy Transfer Between Fluorescently Labled Receptors and a Metallic Surface", *Elsevier B.V.*, Biosensors & Bioelectronics, 17 (2002), pp. 71–78.

H. Sheng, et al., "Nonalloyed Al Ohmic Contacts to $Mg_xZn_{1-x}O$", *Journal of Electronic Materials*, vol. 31, pp. 811–814.

Kourosh Kalantar Zadeh et al., A Novel Love–mode Device based on a ZnO/ST–cut Quartz Crystal Structure for Sensing Applications, *Elsevier Science B.V.*, Sensors and Actuators, A 100 (2002), pp. 135–143.

Sriram Muthukumar, et al., "Selective MOCVD Growth of ZnO Nanotips", *IEEE Transactions on Nanotechnology*, vol. 2, No. 1, Mar. 2003, pp. 50–54.

Jianming Ye, et al., "Piezoelectric Biosensor for Detection of *Salmonella typhimurium*", *Journal of Food Science*, vol. 62, pp. 1067–1086.

Copy of International Search Report from corresponding International Patent Application No. PCT/US03/17822, filed Jun. 6, 2003.

* cited by examiner (a)

MULTIFUNCTIONAL BIOSENSOR BASED ON ZNO NANOSTRUCTURES

CROSS-REFERENCE TO RELATED APPLICATION

This application claims priority to U.S. Provisional Patent Application No. 60/385,884, which was filed on Jun. 6, 2002.

This invention was made with Government support under Grant Nos. NSF ECS-0088549 and NSF CCR-0103096, awarded by the National Science Foundation. Therefore, the Government has certain rights in this invention.

FIELD OF THE INVENTION

This invention relates generally to biosensor technology, and pertains more particularly to novel multifunctional biosensors based on zinc oxide (ZnO) nanostructures for biological, biochemical, chemical and environmental applications.

BACKGROUND OF THE INVENTION

The nanoscale science and engineering have shown great promise for the fabrication of novel nano-biosensors with faster response and higher sensitivity than that of planar sensor configurations, due to their small dimensions combined with dramatically increased contact surface and strong binding with biological and chemical reagents which could have important applications in biological and biochemical research, as well as in environmental monitoring and protection.

ZnO nanostructures have many advantages. As disclosed in U.S. patent application Ser. No. 10/243,269, nanotip arrays made with insulating or conductive ZnO can be fabricated in a controlled manner to produce tips with a uniform size, distribution and orientation. The ZnO nanotips are made using our chemical vapor deposition (CVD)-based method in a simple process at relatively low temperatures as disclosed by S. Muthukumar*, H. Sheng*, J. Zhong*, Z. Zhang*, N. W. Emanaetoglu*, Y. Lu, "Selective MOCVD Growth of ZnO Nanotips", *IEEE Trans. Nanotech,* Vol.2, n.1, pp.50–54 (2003), giving ZnO nanostructures a unique advantage over other wide bandgap semiconductor nanostructures, such as gallium nitride (GaN) and silicon carbide (SiC). Furthermore, through proper doping and alloying, ZnO nanotips can be made as piezoelectric and ferroelectric, transparent and conducting, and magnetic, thus having multifunctional applications.

Recent advances in genetic sequencing methods are leading to an explosion in the area of biotechnology. Many emerging areas of biotechnology are based upon highly-parallel methods for sequencing and detecting DNA, RNA, and proteins. Many of these areas could benefit greatly by leveraging the emerging nanotechnology, but applying it to develop and utilize new analytical tools for biochemical analysis. A need exists to provide novel biological and biochemical sensors, which have higher sensing efficiency and multiple functionality, thereby having significant advantages in comparison to the existing sensor technology.

SUMMARY OF THE INVENTION

It is the primary objective of this invention to address the novel multifunctional biosensor technology based on ZnO nanotips and nanotip arrays.

Particularly, it is an objective of this invention to provide conductivity-based biosensors using semiconductive or conductive ZnO nanotips; to provide field-effect-transistor (FET)-based biosensors by using ZnO nanotips as the gate of the FET; to provide surface acoustic wave (SAW)-based biosensors by integrating ZnO nanotips into SAW devices to form highly sensitive and multichannel biosensors; and to provide bulk acoustic wave (BAW)-based biosensors by integrating ZnO nanotips into BAW devices to form highly sensitive and multichannel biosensors.

As ZnO nanotips can be made semiconducting, transparent and conducting, or piezoelectric, their unique electrical, optical and acoustic properties can serve as the basis for multifunctional sensors. A sensor chip comprising of arrays and combinations of various types of ZnO nanotip-based biosensors also allow for multimodal operation.

DETAILED DESCRIPTION OF THE TECHNOLOGY

A biosensor is a device which is capable of providing analysis of various analytes or biomolecules using biological recognition elements which are combined with a signal transducer. Generally, the sensor will produce a signal that is quantitatively related to the concentration of the analytes.

The biological recognition elements serve to recognize the analytes. These elements include enzymes, microorganisms, tissues, antibodies, receptors, nucleic acids, organelles or whole cells.

Transducers are physical components of the biosensor that respond to the products of the biosensing process and outputs the response in a form that can be amplified, stored or displayed. Biosensing occurs only when the analyte is recognized specifically by the biological element. Biological recognition in vivo at a single cell level is characterized by high sensitivity, fast response, specificity and reversibility.

A "sensor surface" refers to the location upon which a binding partner is immobilized for the purpose of measuring changes in physical properties, such as optical refractive index, electrical conductivity, mass loading, etc. They include, but are not limited to, semiconductor, metal and dielectric surfaces.

ZnO is a wide bandgap semiconductor having a direct bandgap of 3.32 eV at room temperature and can be made semiconducting, piezoelectric, ferroelectric, ferromagnetic, and transparent and conducting through proper doping. ZnO has an exciton binding energy of 60 meV. It is found to be significantly more radiation hard than silicon (Si), gallium arsenide (GaAs), and GaN.

ZnO is a polar semiconductor with the (0002) planes being Zn-terminated and the (000$\bar{2}$) planes being O-terminated. These two crystallographic planes have opposite polarity and hence have different surface relaxations energies. This leads to a higher growth rate along the c-axis. The ZnO film grown on many semiconducting, insulating or metallic substrates have a preferred c-axis orientation normal to the surface. Therefore, ZnO growth results in a pillar like structure called ZnO nanotips on these semiconducting, insulating and metallic substrates, while ZnO grown on R-plane sapphire substrates results in a smooth epitaxial film. The ZnO nanotips can be grown at relatively low temperatures, giving ZnO a unique advantage over other wide bandgap semiconductor nanostructures, such as GaN and SiC.

ZnO is an important multifunctional material, which has wide applications in telecommunications, chemical and biochemical sensors and optical devices. In this application, ZnO nanotips are used as the sensor surface to enhance the immobilization in detection of DNA, protein, and harmful biological agents in the field of biological and biochemical sensors. The use of ZnO nanotip arrays also greatly increases the effective sensing area of the biosensor devices as will be described in greater detail below.

ZnO nanotips can be grown on various substrates. They can also be selectively grown on patterned layers of materials through substrate engineering. Both cases have been disclosed in U.S. patent application Ser. No. 10/243,269.

Figure 1:
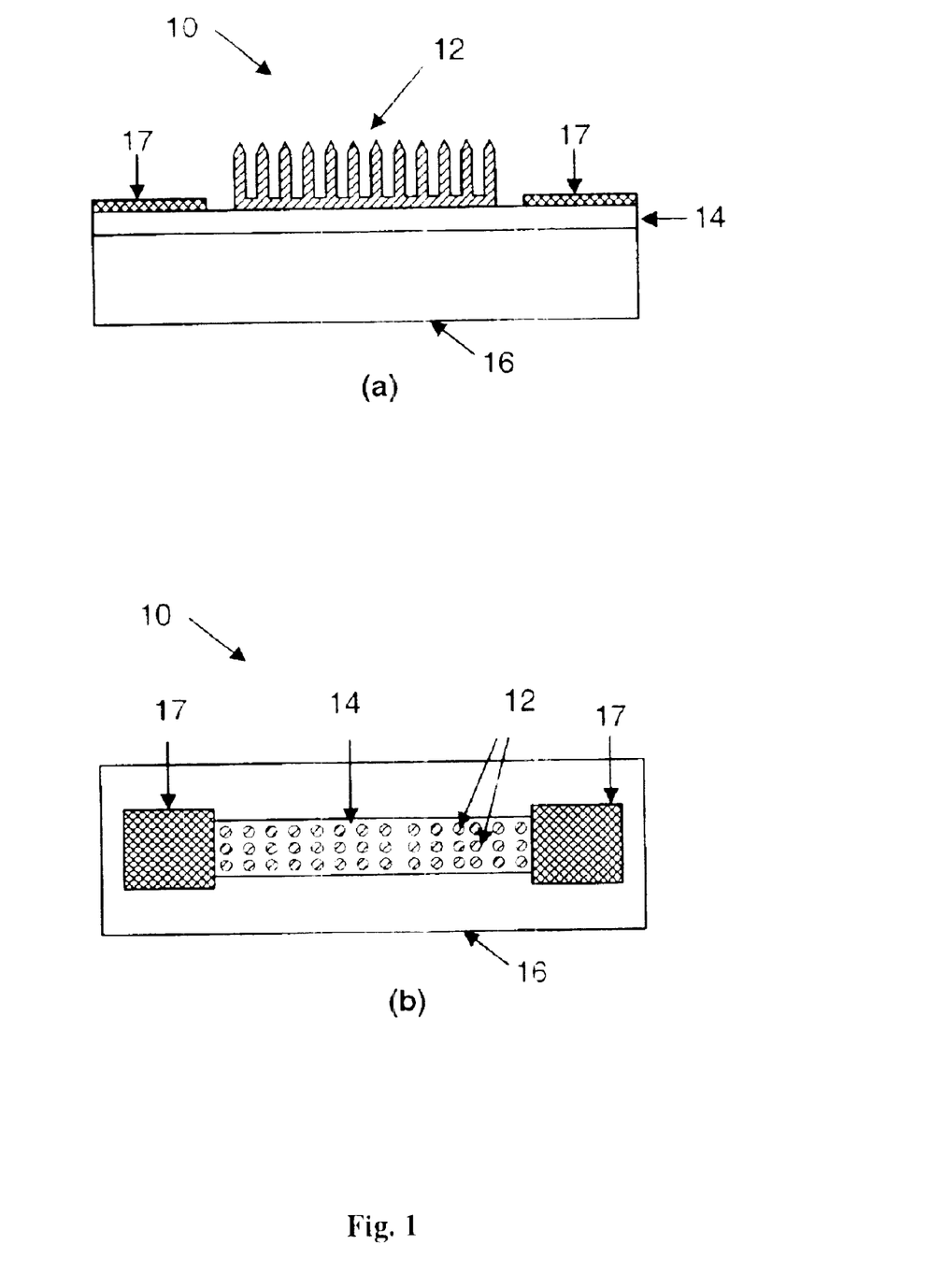
FIG. 1a shows a schematic of a vertical cross-section view of the device structure for the conductivity-based ZnO nanotip biosensor.
FIG. 1b shows a schematic of top view of the conductivity-based ZnO nanotip biosensor structure.

Referring to FIGS. 1a and 1b, a schematic of vertical cross-section view and a top view respectively of a conductivity-based ZnO nanotip biosensor 10 are shown. The biosensor consists of a substrate 16, a conductive thin film 14, a ZnO nanotip array 12 on the conductive thin film 14, and metal electrode pads 17. A reaction between the immobilized species on ZnO nanotips 12 with the target will result in a change in the total change accumulated on nanotips. This change will cause a transient current across the biosensor device, which will be used as the sensor output, as will be described below.

The substrate 16 can be a semiconductor substrate, such as Si or GaAs, in which case the biosensor can be integrated with electronic integrated circuits (ICs). In a second embodiment of the invention, the substrate 16 can be a transparent insulating substrate, such as glass or sapphire, in which case both electrical and optical sensing mechanisms can be used to realize a multifunctional sensor. In a third embodiment of the invention, the substrate 16 can be a piezoelectric substrate, such as quartz or lithium niobate (LiNbO$_3$), in which case the conductivity-based sensor can be integrated with the SAW-based sensor to realize another type of multifunctional sensor as described later in this application.

The conductive thin film 14 has certain conductivity, and it can be a semiconductor, such as Si with properly designed doping level, a metallic thin film, such as gold (Au), a transparent conductive oxide, such as indium tin oxide (ITO), or even the multilayer thin film. The thin film and the metal bond pads are deposited on the substrate 16, then patterned using the standard microelectronic processing techniques.

The ZnO nanotips 12 can be deposited on the substrate 16 and thin film 14 using the technology, but not limited to metal-organic chemical vapor deposition (MOCVD), then patterned by the standard photolithography and etching process.

These ZnO nanotips serve as DNA or protein molecule binding sites. In other words, the ZnO nanotips 12 are preferably bonded with protein or DNA molecules to make conductivity-based biosensors, as will be described in detail below. Specifically, the conductive thin film 14 surface, with ZnO nanotips 12 grown on the top, will be designed and fabricated as conductivity-based biosensors. Preferably a probe is attached to said tip to seek the targeted molecule due to bioreaction. The probe may preferably be attached on a binding site or a target molecule preferably has a probe. Any useful probes preferably such as chemiluscence, fluorescence, etc. The dimensions of the conductive pattern, the aspect ratio and doping level of the ZnO nanotips, are optimized to enhance the sensitivity. Due to depletion or accumulation of carriers in the nanotips as a result of bioreactions, the conductance of the patterned tip arrays will change significantly. The depletion (accumulation) of the nanotips will result in a transient current across the line. The amplitude of this current will be a function of the amount of target material detected, and the duration to the reaction time. The similar effect was recently demonstrated using Boron doped silicon nanowire biosensors for detection of protein-protein interactions by Y. Cui, Q. Wei, H. Park, and C. M. Lieber, "Nanowire nanosensors for highly sensitive and selective detection of biological and chemical species", *Science* 293, 1289 (2001).

If a transparent substrate, either insulating or piezoelectric, is used, the conductivity based ZnO nanotip biosensor 10 can be operated in optical mode simultaneously with the conductivity mode. ZnO has an optical cut-off wavelength of approximately 373 nm at room temperature. This optical cut-off wavelength can be extended by using its ternary compound, magnesium zinc oxide (Mg$_x$Zn$_{1-x}$O). As Mg$_x$Zn$_{1-x}$O is transparent down to ~240 nm (for x=0.6), the changes in the optical absorption characteristics before and after the bioreactions can also be detected and analyzed. During operation, the device is illuminated with ultra-violet (UV) light from one side (top or bottom), and the light is detected on the other side. Changes in the UV absorption spectra are unique to each chemical, allowing identification of the reactant species. Further more, if the tip array is coated with a thin layer of Au (<100A), it can also be functional for fluorescence biosensing as shown by V. H. Perez-Luna, S. Yang, E. M. Rabinovich, T. Buranda, L. A. Sklar, P. D. Hampton, and G. P. Lopez, "Fluorescence biosensing strategy based on energy transfer between fluorescently labeled receptors and a metallic surface", *Biosens Bioelectron.* 17, 71 (2002).

In another embodiment of the present invention, there is disclosed a second type of device, which is a ZnO nanotip-gate field-effect-transistor (FET). FETs have been used for chemical sensors. In a FET, a voltage bias applied to the gate of a FET will modulate the current flowing between its source and drain. There are two major types FETs which can be used with biosensors. The first is a metal-insulator-semiconductor FET (MISFET), composed of a metal gate deposited on a gate insulator layer, which is deposited on the semiconductor. The second is a metal-semiconductor FET (MESFET), composed of a metal gate directly deposited on the semiconductor. If the gate insulator is specifically an oxide, the MISFET device is known as a metal-oxide-semiconductor FET (MOSFET).

An FET type of biosensor can be realized by depositing ZnO nanotips on the gate region of the FET. Such an FET can be a current existing Si MOSFET, GaAS MESFET, etc. The surface charge changes occurring with the target on the ZnO nanotips will result in a potential difference between the gate and the substrate, and modulate the current flowing between the source and the drain. Unlike the resistor-type conductivity-based sensor described above, the FET type sensor can be used for both transient and steady-state current measurements, making it a more flexible device.

Figure 2:
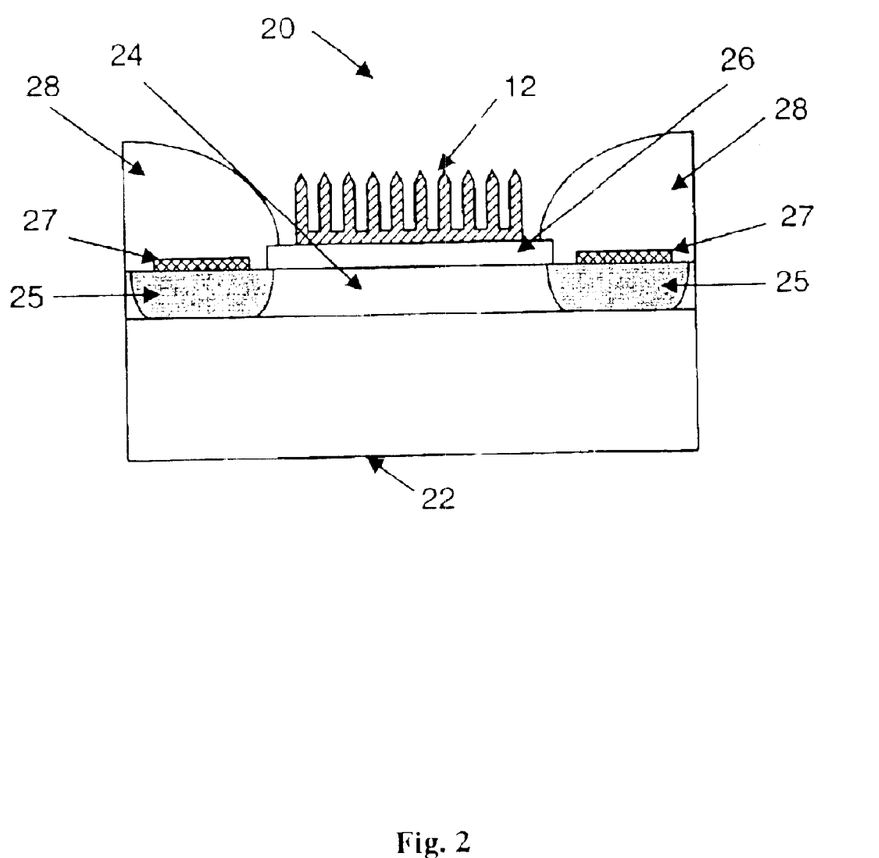
FIG. 2 shows a schematic of a vertical cross-section of a ZnO nanotip gate metal-insulator-semiconductor field effect transistor (MISFET).

More specifically, a novel transparent FET sensor is composed of a ZnO nanotip gate and a ZnO FET. Referring to FIG. 2, there is shown a schematic of a vertical cross-section view of nanotip gate ZnO MISFET biosensor 20. It is composed of a R-plane sapphire (R—$Al_2O_3$) substrate 22, a semiconductor ZnO thin epitaxial layer as a channel 24, doped ZnO source and drain regions 25, a gate insulator 26, metal electrodes 27 to the source and drain regions 25, the ZnO nanotips 12 deposited on the gate, and an encapsulation layer 28 to protect the device except the nanotip gate area.

In this device, $n^+$-ZnO 25 regions serve as the source and the drain. When Al is used for the metal contacts 27, it will heavily dope the ZnO thin film 24 under it, resulting in good non-alloyed ohmic contact as developed in H. Sheng, N. W. Emanetoglu, S. Muthukumar, and Y. Lu, "Non-alloyed Ohmic Contacts to $Mg_xZn_{1-x}O$", *J. Electronic Materials*, 31 (2002). This process will be used to simultaneously dope the source and drain regions and form their ohmic contacts in the ZnO MISFET structure. A thin insulation layer 26 will be deposited, and patterned on top of the n-ZnO 24 thin film. Candidate insulators 26 include, but are not limited to, silicon dioxide ($SiO_2$) and magnesium zinc oxide ($Mg_xZn_{1-x}O$) with more than 50% Mg mole percentage composition. The device will be protected with the encapsulating layer 28 from the chemical environments it operates in. The ZnO nanotips 12 will be grown on the insulator layer 26, patterned and etched to serve as the nanotip-gate.

The operation of the ZnO nanotip-gate transparent MISFET 20 is simple. When a biological reaction occurs with the target at the ZnO nanotips 12, the negative surface charge will change, inducing with a potential difference between the gate and the ZnO film. This potential difference will change the conductivity in the n-type ZnO channel 24 under the gate insulator 26, resulting in a change in the current between the source and the drain regions 25.

As in the conductivity-type ZnO nanotip biosensors 10 described above, the ZnO nanotip-gate transparent MISFET biosensor 20 can be operated in optical mode simultaneously with electrical mode. ZnO nanotips, R—$Al_2O_3$, $SiO_2$ and $Mg_xZn_{1-x}O$ (0.5<x<1) are all transparent to visible light, therefore allow the sensor to be operated in optical mode.

Figure 3:
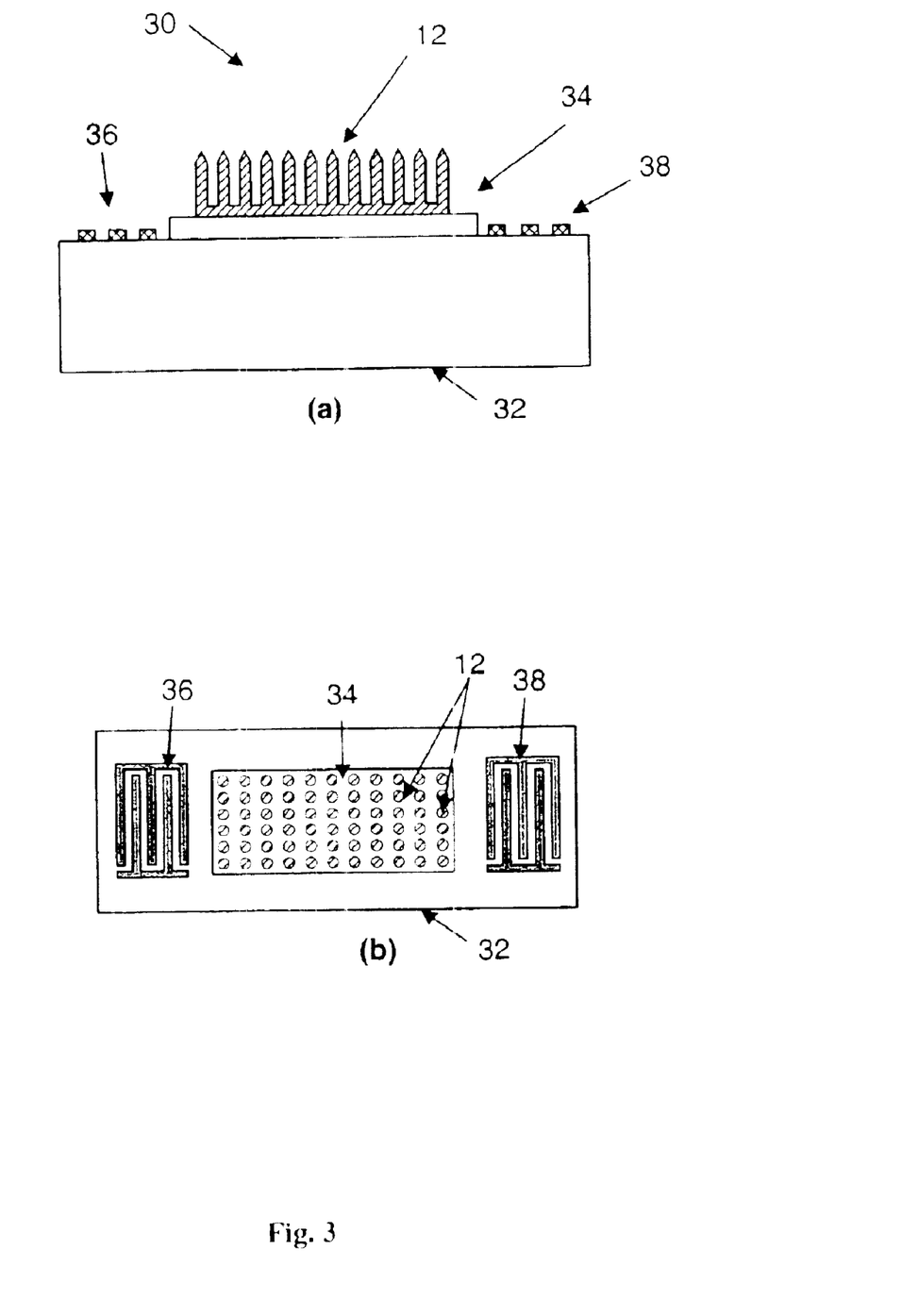
FIG. 3a shows a schematic of a vertical cross-section view of a ZnO nanotip SAW sensor.
FIG. 3b shows a schematic of a top view of ZnO nanotip SAW sensor.

In another embodiment of the present invention, there is disclosed a third type of device which integrates piezoelectric ZnO nanotips with SAW biosensors. Referring to FIGS. 3a and 3b, there is shown a schematic of a vertical cross-section view and a schematic of a top view respectively of ZnO nanotip SAW biosensor 30. The ZnO nanotip SAW biosensor is composed of a piezoelectric substrate 32, an insulating amorphous layer 34, a metal input interdigital transducer (IDT) 36, a metal output IDT 38, and the ZnO nanotips 12.

The piezoelectric substrate 32 can be, but is not limited to, quartz, $LiNbO_3$, lithium tantalate ($LiTaO_3$), etc. An insulating amorphous layer 34 is deposited on the piezoelectric substrate and patterned using the standard microelectronic processing techniques. This insulating amorphous layer can be, but is not limited to, $SiO_2$ or $Si_3N_4$.

The ZnO nanotips 12 are deposited on the surface of the insulating layer 34 using MOCVD, or other deposition technology, then patterned and etched to define the nanotip coverage area. The metal IDTs 36 and 38 are then deposited and patterned using standard microelectronic processing techniques. The metal of choice is Al, but other metals can also be used.

The ZnO nanotip SAW sensor device 30 operates similarly to a planar SAW biosensor. A dualchannel biosensor consisting of two identical devices, one without target coating serving as the reference and the other with target coating serving as the sensor, are used together. As the target binds with the ZnO nanotips 12 on the sensor device, mass loading of the sensor will result in a decrease of the phase velocity under the ZnO nanotips. This will results in a phase difference between the output signals of the reference and the sensor devices. The use of ZnO nanotips dramatically enhances the immobilization of DNA, protein and other small biomolecules, therefore the sensitivity of the biosensors. Our preliminary experimental results demonstrate that the immobilization rate of ZnO nanotips is over thirty times higher than that of smooth surface. It is well known that the rough surface will increase the viscosity of the sensing media on the acoustic path and deteriorate the device performance. Therefore, the ZnO nanosize tip-type structures 12 will have higher electromechanical coupling coefficient to compensate the increased propagation loss as disclosed by K. K. Zadeh, A. Trinchi, W. Wtodarski, and A. Holland, "A novel love-mode device based on a ZnO/ST-cut quartz crystal structure for sensing applications", *Sensors and Actuators A* 3334, 1 (2002).

In the refinement of the invention, the SAW based ZnO nanotip biosensor 30 can be operated in optical and SAW modes simultaneously, if a transparent piezoelectric substrate, such as quartz or $LiNbO_3$, is used. As in the conductive-type nanotip biosensors 10, the sensor 30 is illuminated with UV light on one side (either top or bottom) and the transmitted UV light is detected at the other side. The UV absorption spectrum can be used to identify the reactant species.

In another refinement of the invention, the SAW based ZnO nanotip biosensor 30 can be operated in electrical and SAW modes simultaneously, if the insulating layer structure is replaced with the resistor-type conductive ZnO nanotip biosensor structure.

in a further refinement of the invention, the ZnO nanotips 12 can be combined with the monolithically integrated tunable SAW (MITSAW) sensors disclosed previously (U.S. Pat. No. 6,559,736 and U.S. patent application Ser. No. 09/905,205), to enhance their performance.

In preliminary work, SAW delay lines are fabricated on 128° Y-cut $LiNbO_3$ with a ZnO nanotip/$SiO_2$ layer structure deposited on the propagation path. The IDT structure of this prototype device consists of 50 pairs of electrodes, 963 $\mu$cm long, 3 $\mu$m wide and 3 $\mu$m apart from each electrode for both IDTs. The phase velocity (v) of the SAW on the 128° Y-cut $LiNbO_3$ is 3668 m/s, and the wavelength ($\square$) of the test pattern is 12 $\mu$m. From the equation $f_c=v/\square$, the expected center frequency is 305 MHz. The bandwidth is $BW_{3db}=(0.9/N_p)*f_c=0.9*305/50=5.49$ MHz. On the propagation path of the prototype devices, the sensor region has 600 nm ZnO nanotip/100 nm $SiO_2$ is 1116 $\mu$m long and 594 $\mu$m wide. Furthermore, the dual channel (reference and sensor channels) device is tested using an Agilent 8573D Network Analyzer. The reference channel has no protein bonding and the sensor channel is bonded with 100 ng protein on the ZnO nanotip over an area of $6.629\times10^{-3}$ $cm^2$.

Figure 4:
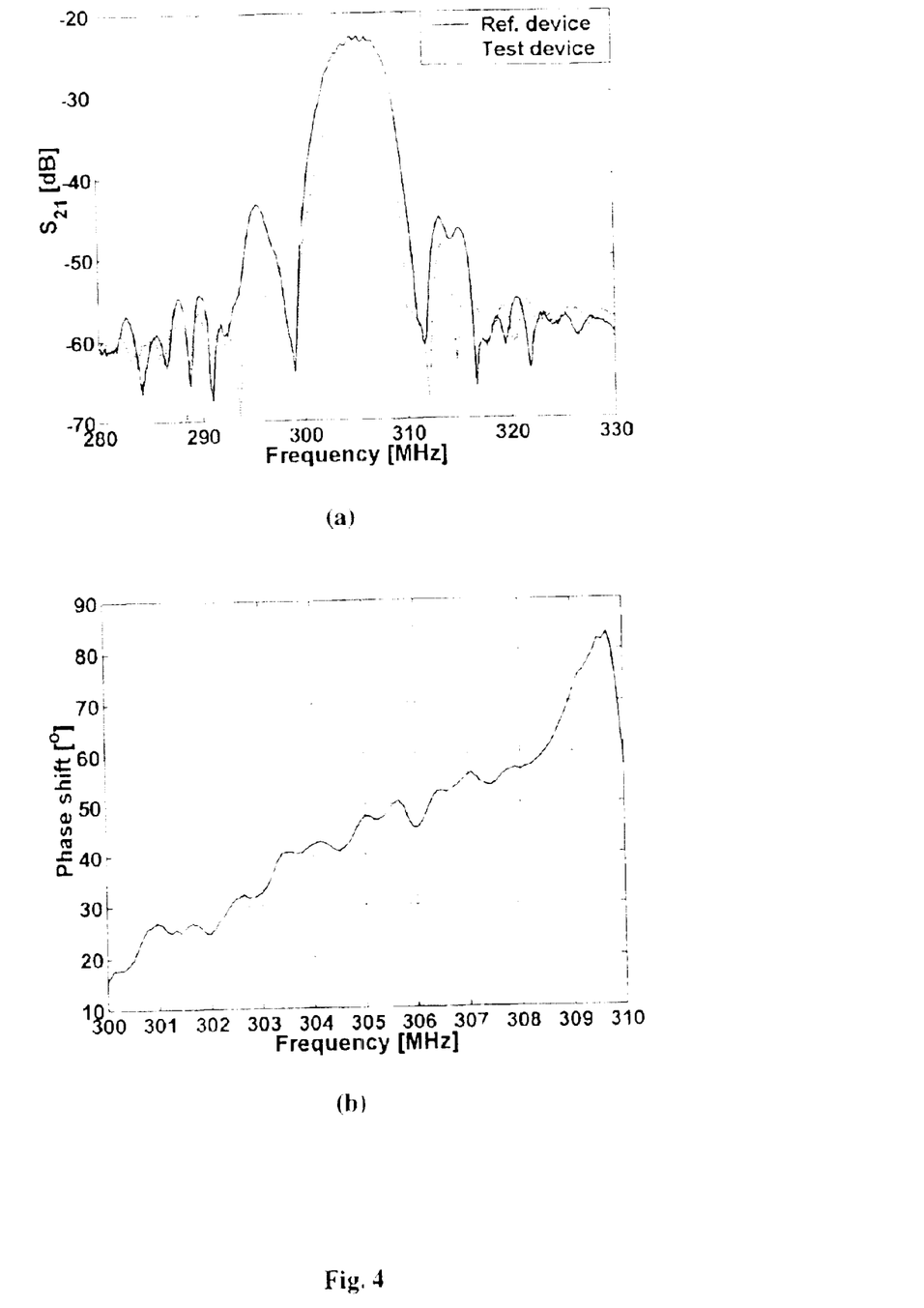
FIG. 4a shows an example of transmission spectra as a function of frequency for test ZnO nanotip SAW sensor devices.
FIG. 4b shows a plot of a phase shift as a function of frequency between the reference and test ZnO nanotip SAW sensor devices.

The frequency responses of the reference sensor device and the actual test sensor device are shown in a graph shown in FIG. 4a. The X-axis is the frequency and the Y-axis is the $S_{21}$ transmission spectra of reference and sensor device. As shown in FIG. 4a, the sensor device has a shift to lower frequency compared with the reference device. An additional insertion loss of 6.14 dB is observed for the protein bonded sample. However, the insertion loss shift depends on a number of factors, and by itself is not a good sensing mechanism. Instead, the phase shift of the signal is preferred for accurate and repeatable measurements.

FIG. 4b shows a graph displaying a phase difference between the reference and sensor prototype devices. The X-axis is the frequency and Y-axis is the phase difference between the reference and sensor device. As shown in FIG. 4b, the sensor device has a 47.68° phase shift at the center frequency 305 MHz compared with the reference device. The phase shift increases with increasing frequency, due to the different velocity dispersion characteristics of the SAW propagating in the reference and sensor channels. The phase velocity decreases with increasing frequency, as sensitivity increases with frequency. This phase velocity decrease results with a larger phase difference between the sensor and reference devices with increasing frequency. Nominally, the phase shift should be a monotonically increasing function. However, due to such factors as electromagnetic feedthrough and triple transit interference (TTI), the phase response has ripples. The impact of these secondary effects on sensor performance can preferably be minimized. The proof-of-concept device uses an unoptimized SAW delay line structure. Narrower bandwidths and larger phase shifts can be achieved by optimizing the device parameters and proper choice of substrate.

Figure 5:
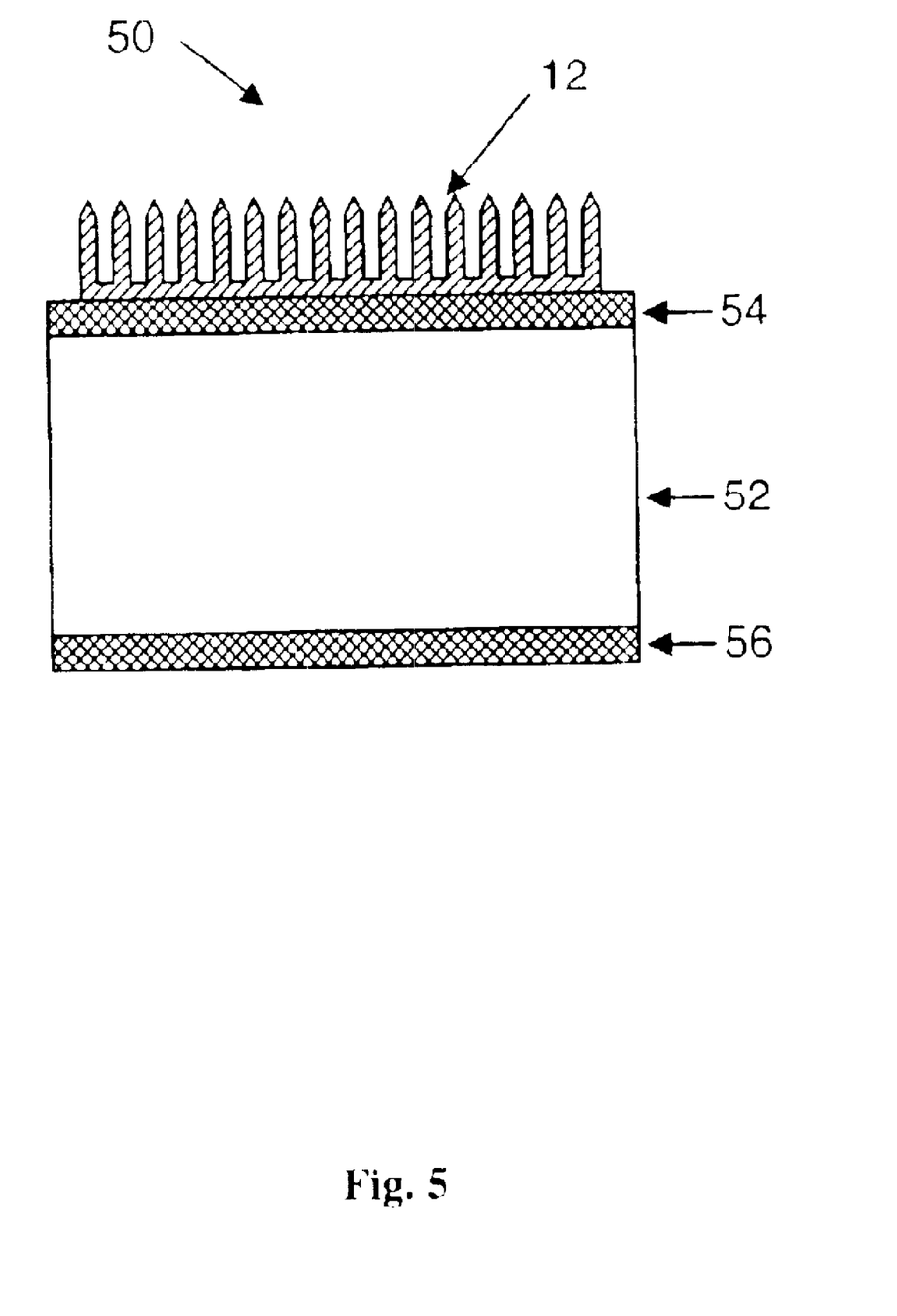
FIG. 5 shows a schematic of a vertical cross-section of a ZnO nanotip BAW sensor.

In another embodiment of the present invention, there is disclosed a fourth type of device which integrates piezoelectric ZnO nanotips with BAW biosensors. Referring to FIG. 5, there is shown a schematic of a vertical cross-section view of a ZnO nanotip BAW biosensor 50. The ZnO nanotip BAW biosensor 50 is composed of a piezoelectric material 52, a metal top electrode 54, a metal bottom electrode 56 and ZnO nanotips 12.

The piezoelectric material 52 can be, but is not limited to, quartz, $LiNbO_3$, $LiTaO_3$, etc. The metal top 54 and bottom 56 electrodes are deposited and patterned using the standard microelectronic processing techniques.

The ZnO nanotips 12 are deposited on the top metal electrode surface using MOCVD, or other deposition technology, and then patterned and etched to define the nanotip coverage area of the BAW sensor.

In a further embodiment of the ZnO nanotip BAW sensor 50, the center area of the top surface of the piezoelectric substrate is not metallized. The ZnO nanotips 12 are deposited on the bare piezoelectric substrate surface 52, so that the top metal electrode 54 surrounds, but does not contact the ZnO nanotips 12.

The ZnO nanotip BAW sensor 50 operates similarly to a BAW resonator device. The BAW resonator will resonate at a specific frequency determined by the piezoelectric substrate material properties and thickness. When bonding of the target occurs on the ZnO nanotips 12, mass-loading results with a shift in the resonance frequency of the resonator, directly proportional to the amount of target material bonded to the ZnO nanotips 12.

In a further embodiment of the ZnO nanotip BAW sensor 50, the crystal resonator of FIG. 5 can be replaced with a thin film resonator structure, including, but not limited to, air gap resonators, solidly mounted resonators and membrane (Film Bulk Acoustic Resonator or FBAR) resonators. The thin film resonator structure includes, but not limited to, an air-gap structure on top surface of the substrate, a membrane structure on the substrate and an acoustic mirror on top surface of the substrate.

In a further embodiment of the present invention, there is disclosed a biochip consisting of ZnO nanotip array as biosensors to simultaneously detect a number of different biological information. For certain clinical and scientific applications it is desirable to use multiple biosensors on a chip for simultaneous detection of several biomolecular targets. For this purpose a biosensor chip having multiple detection units for different targets. As described above, both types of biosensor devices with 1D or 2D arrays on a chip can be fabricated through regular microelectronics fabrication processes.

The current invention presents a new biochemical sensor technology with high sensitivity and multimodal operation capability. The sharp ZnO nanotips 12 on four type devices, as discussed above, provide the favorable binding sites to enhance the immobilization, and increase the effective sensing area, therefore, improve the sensing and detection efficiency. The changes in electrical conductivity, or/and optical absorption, or/and fluorescence in conductive and semiconductive ZnO nanotips will be used to sense the targeted biochemical reactions. The ZnO nanotip SAW or BAW sensors possess both the advantages of SAW or BAW, and nanostructured biosensors.

The ZnO biosensors described above are used to detect RNA-DNA, DNA-DNA, protein-protein, protein-DNA, and protein-small molecule interactions taking advantage of the enhancement of immobilization of DNA, protein molecules on the ZnO nanotips. The optimum immobilization conditions can be used for the biosensors to further enhance their sensitivities and specify the target molecules.

For DNA immobilization, a solution of avidin is applied to the clean surface of ZnO nanotips 12, and then biotinylated oligonucleotide will be attached to the modified nanostructured surface as disclosed by G. Marrazza, I. Chianella, and M. Mascini, "*Disposable DNA electrochemical sensor for hybridization detection*", Biosens Bioelectron. 14, 43 (1999). The modified nanostructured surface includes the ZnO surface 12 initially coated with Cr, Ti, etc., to help the subsequent Au layer wet the surface. The Au film is then deposited and modified with thiol/dextran, which in turn will allow the covalent attachment of avidin as disclosed by S. Tombelli, M. Mascini, L. Braccini, M. Anichini, and A. P. Turner, "*Coupling of a DNA piezoelectric biosensor and polymerase chain reaction to detect apolipoprotein E polymorphisms*", Biosens Bioelectron. 15, 363 (2000). Thiolated DNA oligonucleotides are covalently attached to mercaptosilane-derivatised surface via succinimidyl 4-[malemidophenyl]butyrate (SMPB) crosslinker as disclosed by T. A. Taton, C. A. Mirkin, and R. L. Letsinge, "*Scanometric DNA array detection with nanoparticle probes*", Science 289, 1757 (2000) and L. A. Chrisey, G. U. Lee, and C. E. O'Ferrall, "*Covalent attachment of synthetic DNA to self-assembled monolayer films*", Nucleic Acids Res. 24, 3031 (1996). The Thiolated DNA oligonucleotides can serve as the biological recognition elements which recognize the analytes.

For testing the efficiency of DNA immobilization procedures, model oligonucleotides with a radioisotope/fluorescent label are preferably used. For testing and calibration of DNA/RNA ZnO nanotip biosensors, a series of complementary pairs of oligonucleotides (20 and 50 nucleotides in length) which are 30, 50 and 70% GC-reach are synthesized having different percents of complementarity (from no to several mismatches). Basically, preferably light with a particular wavelength (λ) is passed through the transparent ZnO nanotip 12 and one member of each pair of oligonucleotides is immobilized on a surface of ZnO biosensor 10 and the device is tested in a series of hybridization experiments with the corresponding targets. Different hybridization conditions, as well as different RNA targets are evaluated. These targets may preferably be labeled. As an example of the practical application two sets of experiments are conducted with specific targets. One such target is detection of cold-shock inducible cspA mRNA from *E. coli*. Some major advances in understanding of the regulatory mechanisms of cspA expression have been made as disclosed by S. Phadtare, J. Alsina, and M. Inouye, "*Cold-shock response and cold-shock proteins*", *Curr Opin Microbiol.* 2, 175 (1999). Another is detection of mutations in the BRCA1 gene. This gene is responsible for 40% of breast cancer cases and 80% of breast-ovarian cancer cases as disclosed by M. O. Nicoletto, M. Donach, A. D. Nicolo, G. Artioli, G. Banna, and S. Monfardini, "*BRCA-1 and BRCA-2 mutations as prognostic factors in clinical practice and genetic counseling*", *Cancer Treat. Rev.* 27, 295 (2001). We preferably use oligonucleotides complementary to the 185delAG and 188del11 mutations of the gene, which are the most common in all reported cases as disclosed by D. Tong, M. Stimpfl, A. Reinthaller, N. Vavra, S. Mullauer-Ertl, S. Leodolter, and R. Zeillinger, "*BRCA1 gene mutations in sporadic ovarian carcinomas: detection by PCR and reverse allelespecific oligonucleotide hybridization*", *Clin. Chem.* 45, 976 (1999). So, if we see binding, i.e. we get a signal such as fluorescent light, we know that patient's DNA strength hits breast cancer mutation.

For protein immobilization, strategies similar to those of DNA are used. As mentioned above, proteins may have strong affinity to ZnO surface 12. The Au coated ZnO surface is modified with thiol/dextran and activated by N-hydroxysuccinimide and N-(3-dimethylaminopropyl)-N-ethylcarbodiimide allowing covalent attachment of the protein as disclosed by N. Barie and M. Rapp, "*Covalent bound sensing layers on surface acoustic wave (SAW) biosensors*", *Biosens Bioelectron* 16, 979 (2001). The ZnO surface 12 will be precoated with polyethylenimine and the protein will be crosslinked to the surface via glutaraldehyde as disclosed by J. Ye, S. V. Letcher, and A. G. Rand, "*Piezoelectric biosensor for the detection of Salmonella typhimurium*", *J. Food. Sci.* 62, 1067 (1997). Also bromocyano-immobilization will be preferably modified in which the shilding layer (polyimide or polystyrene) will be first loaded on the ZnO surface 12, following CNBr activation and coupling the protein as disclosed by T. Wessa, M. Rapp, and H. J. Ache, "*New immobilization method for SAW-biosensors: covalent attachment of antibodies via CNBr*", *Biosens Bioelectron* 14, 93 (1999).

In another case, for protein immobilization, a histidine kinase called EnvZ was used. The protein was first phosphorylated with γ-[$^{32}$P] ATP and solution of $^{32}$P-labled EnvZ was loaded on the nanotips grown on a square glass plate (5×5 mm). After incubation for 90 minutes, plates were washed extensively at room temperature by changing the washing buffer solution five times. The radioactivity of the plate was then measured. More than 90% of the protein was retained on the surface, indicating a strong affinity of the protein to the ZnO surface. It was also found that EnvZ attached on the nanotip surface retained its biochemical property, as approximately 80% of $^{32}$P radioactivity was released when the plate was incubated in a solution containing OmpR, an EnvZ substrate, but no radioactivity was released in the presence of other proteins. This model system is preferably used for analysis of protein-protein interactions via optical techniques, since EnvZ forms a stoichiometric complex with OmpR.

Fluorescence resonance energy transfer (FRET) is a quantum mechanical process wherein excitation energy is transferred from a donor fluorophore to an appropriately positioned acceptor positioned acceptor fluorophore without emission of a photon. Energy can be transferred this way only over a very limited distance, and the efficiency of the energy transfer varies inversely with the sixth power of the distance separating the donor and acceptor. One of the most important uses of FRET spectroscopy is to study protein-protein interactions.

For testing protein immobilization in addition of a histidine kinase we use preferably as a model, calmodulin (CaM) fused with two mutant proteins, CFP (a mutant of green fluorescent protein, GFP; cyan fluorescent protein) at the N-terminal end and YFP (another mutant of GFP; yellow fluorescent protein) at the C-terminal end as disclosed by A. Miyawaki, J. Liopis, R. Heim, J. M. McCaffery, J. A. Adams, M. Ikura, and R. Y. Tsien, "*Fluorescent indicators for Ca2+ based on green fluorescent proteins and calmodulin*", *Nature* 388, 882 (1997). This allows us to easily determine concentration of the protein by measurement of fluorescent intensity. Moreover, CaM protein is termed "cameleon", since it responds to $Ca^{++}$ causing FRET (fluorescent resonance energy transfer) as mentioned above. It is critical to observe whether $Ca^{++}$ is close enough to calmodulin (CaM), in order for them to interact. Again, preferably light with a particular λ (i.e. light capable of exciting the GFP) is passed through transparent ZnO nanotip 12. If the green fluorescent protein fluoresces at its characteristic λ, there is no protein interaction since the protein distance is greater than a specific amount and therefore no FRET occurs. However, if the calmodulin and $Ca^{++}$ are close enough (within FRET proximity) to interact, the GFP is excited but does not emit a photon. Preferably, a sensitized emission from $Ca^{++}$ occurs, so FRET occurs. The effect can be monitored directly on the ZnO sensor 10. Since the ZnO film is transparent, the cameleon-bound ZnO film can be excited from the bottom and the intensity of the emission spectra recorded. The use of cameleons allows us to evaluate the ZnO sensor 10 performance preferably by two mechanisms such as electrical (conductivity) and optical (fluorescence), or acoustic (SAW) and optical (fluorescence). The FRET method monitors real-time protein-protein interaction and/or conformational changes. Therefore, the comparison of our acoustic wave/conductivity measurements with FRET data helps to evaluate signal responsiveness.

The ZnO DNA and protein nanotip array based sensors in this application will further benefit to explore genome-wide gene expression for molecular diagnostics, drug target discovery, and validation of drug effects. The ZnO nanotip-based biosensors can also be applied to development of new methods for the prevention, diagnosis and treatment of diseases. Furthermore, the application of ZnO and its nanostructure-based biosensors can be extended to detection of toxic biochemical agents and hazardous chemicals against bioterrorism and environmental monitoring and protection. Unlike other sensor technologies, ZnO biosensors can operate in multimodes due to its multifunctional material properties (semiconductor, piezoelectric, transparent and conductive, etc.). Nanotips made from ZnO and its ternary compound can be used for UV absorption and fluorescence detection. ZnO nanotip arrays can be highly dense for diagnostic kits and flow-through systems, including ZnO UV biotesting bench (containing emitters, detectors, modulators, and filters), gene chip, lab-on-a chip and living-cell chip.

While the invention has been described in relation to the preferred embodiments with several examples, it will be understood by those skilled in the art that various changes may be made without deviating from the fundamental nature and scope of the invention as defined in the appended claims.

What is claimed is:

1. A conductivity mode ZnO nanotip biosensor device comprising:
   a substrate;
   a layer of conductive thin film and metal bond pads deposited and patterned on said substrate; and
   ZnO nanotips deposited on said substrate and on said film creating a conductive pattern of tip arrays on said film, wherein said ZnO nanotips serve as DNA or protein molecule or small biomolecule binding sites.

2. The biosensor device of claim 1 wherein said substrate is an insulating substrate.

3. The biosensor device of claim 1 wherein said substrate is a piezoelectric substrate.

4. The biosensor device of claim 1 wherein said conductive film is a semiconductor.

5. The biosensor of claim 1 wherein said ZnO nanotips are used for immobilization of DNA or protein molecules to enhance detection of the corresponding targeted DNA, protein or small biomolecules.

6. The biosensor of claim 5 wherein surface charge of the patterned tip arrays changes due to a biological and biochemical reaction of the immobilized DNA, protein molecules or small biomolecules on the ZnO nanotips with the corresponding targeted DNA or protein molecules.

7. The biosensor device of claim 1 wherein said substrate is transparent, thereby allowing said device to be operable in optical mode simultaneously with the conductivity mode.

8. The biosensor device of claim 7 further comprising:
   magnesium zinc oxide nanotips deposited on said transparent substrate for UV absorption biosensing, wherein upon illumination of UV light on said device, change in UV absorption is detected due to a biological or biochemical reaction of the immobilized DNA or protein molecules or small biomolecules on the ZnO nanotips with corresponding targeted DNA or protein molecules.

9. The biosensor device of claim 7 further comprising:
   a layer of gold coated on the ZnO nanotips for fluorescence biosensing wherein upon illumination of light on said device, the fluorescence is detected due to a biological or biochemical reaction of the immobilized DNA or protein molecules or small biomolecules on the ZnO nanotips with corresponding targeted DNA or protein molecules or small biomolecules.

10. The biosensor device of claim 1 operates in multiple modes due to multifunctional material properties of the ZnO nanotips such as semiconducting, piezoelectric, or transparent and combinations thereof.

11. A ZnO nanotip-gate field effect transistor biosensor device comprising:
    a semiconductor FET structure including a source region, a drain region and a gate region;
    ZnO nanotips deposited on said gate region; and
    an encapsulating layer deposited on surface of the device where there are no ZnO nanotips.

12. The device of claim 11 wherein said ZnO nanotips serve as DNA or protein molecule binding sites to detect presence of the DNA, protein molecules or small biomolecules to be targeted.

13. The device of claim 11 wherein upon said detection of the targeted molecules, a change occurs in the surface charge of the ZnO nanotip-gate resulting in a change in the channel conductance, therefore, a current change between the source and the drain.

14. The device of claim 11 wherein said FET structure comprises a MOSFET.

15. The device of claim 11 wherein said structure comprises GAs MESFET.

16. A ZnO nanotip-gate transparent field effect transistor (FET) biosensor device comprising:
    a substrate
    a semiconductor epitaxial layer grown on top of said substrate;
    a source region, a drain region and a channel between said regions situated in the semiconductor epitaxial layer;
    a gate dielectric layer deposited on top of said channel region;
    metal electrodes deposited on top of said source and drain regions;
    ZnO nanotips deposited on top of said gate dielectric layer to serve as the ZnO nanotip-gate; and
    an encapsulating layer deposited on surface of the device where there are no ZnO nanotips.

17. The transparent FET biosensor device of claim 16 wherein said substrate is insulating substrate and transparent to the wavelength less than 240 nm.

18. The device of claim 16 wherein said semiconductor epitaxial layer is a wide-band gap semiconductor material comprising AlN, GaN, $Al_xGa_{1-x}N$, SiC, ZnO, $Mg_xZn_{1-x}O$, or their heterostructures and combinations thereof.

19. The device of claim 16 wherein said ZnO nanotips serve as DNA, protein molecule or small biomolecule binding sites to detect presence of the DNA, protein molecules or small biomolecules to be targeted.

20. The device of claim 19 wherein upon said detection of the targeted molecules, surface charge of the ZnO nanotip-gate changes, causing a change in conductance of said channel, thereby resulting in a change in current between the source and the drain regions.

21. The device of claim 16 wherein said substrate, wide band gap semiconductor, and ZnO nanotip-gate are transparent, thereby allowing said device to be operable in optical mode simultaneously with electrical mode.

22. The device of claim 16 wherein said semiconductor epitaxial layer is ZnO.

23. The device of claim 22 wherein said substrate is sapphire.

24. The device of claim 22 where in said channel layer is ZnO, n-type ZnO epitaxial layer, or $ZnO/Mg_xZn_{1-x}O$ heterostructure and combinations thereof.

25. The device of claim 22 wherein said source and drain regions are heavily doped with ZnO film.

26. The device of claim 22 wherein said source and drain regions are heavily doped with n-type ZnO film.

27. The device of claim 22 wherein said ZnO nanotips serve as DNA or protein molecule binding sites to detect presence of the DNA, protein molecules or small biomolecules to be targeted.

28. The device of claim 22 wherein upon said detection of the targeted molecules, surface charge of the ZnO nanotip-gate changes, causing a change in conductance of said channel, thereby resulting in a change in the current between the source and the drain regions.

29. The device of claim 22 wherein said substrate, ZnO semiconductor film, and ZnO nanotip-gate are transparent, thereby allowing said device to be operable in optical mode simultaneously with electrical mode.

30. A ZnO nanotip-gate metal-semiconductor field effect transistor biosensor device comprising:
a substrate;
a semiconductor epitaxial layer grown on top of said substrate;
a source region, a drain region and a channel said regions situated in the semiconductor epitaxial layer;
a metal gate layer deposited on top of said channel region, resulting in a Schottky contact to said channel region;
metal electrodes deposited on top of said source and drain regions;
ZnO nanotips deposited on top of said metal gate layer to serve as the ZnO nanotip-gate; and
an encapsulating layer deposited on surface of said device where there are no ZnO nanotips.

31. The device of claim 30 wherein said semiconductor epitaxial layer is a wide-band gap semiconductor material comprising AlN, GaN, $Al_xGa_{1-x}N$, SiC, ZnO, $Mg_xZn_{1-x}O$, or their heterostructures and combinations thereof.

32. The device of claim 30 wherein said ZnO nanotips serve as DNA, protein molecule or small biomolecule binding sites to detect presence of the DNA, protein molecules or small biomolecules to be targeted.

33. The device of claim 30 wherein upon said detection of the targeted molecules, surface charge of the ZnO nanotip-gate changes causing a change in the conductance of said channel, thereby resulting in a change in current between the source and the drain regions.

34. The device of claim 30 wherein the said semiconductor epitaxial layer is ZnO.

35. The device of claim 34 wherein said substrate is sapphire.

36. The device of claim 34 where in said channel layer is ZnO, n-type ZnO epitaxial layer, or $ZnO/Mg_xZn_{1-x}O$ heterostructure, and combinations thereof.

37. The device of claim 34 wherein said source and drain regions are heavily doped with ZnO.

38. The device of claim 34 wherein said source and drain regions are heavily doped with n-type ZnO film.

39. The device of claim 34 wherein said ZnO nanotips serve as DNA, protein molecule or small biomolecule binding sites to detect presence of the DNA, protein molecules or small biomolecules to be targeted.

40. The device of claim 34 wherein upon said detection of the targeted molecules, surface charge of the ZnO nanotip-gate changes causing a change in the conductance of said channel, thereby resulting in a change in the current between the source and the drain regions.

41. A ZnO nanotip SAW biosensor device, comprising:
a piezoelectric substrate;
an insulating amorphous layer deposited on said substrate;
zinc oxide nanotips deposited and patterned on said layer, wherein said combination of the ZnO nanotips and the layer structure is engaged on a SAW propagation path and said ZnO nanotips serve as DNA, protein molecule or small biomolecule binding sites, and metal input and output interdigital transducers deposited on the substrate.

42. The device of claim 41 wherein upon binding of the targeted molecules with said ZnO nanotips causes a mass loading on the SAW path resulting in a decrease of phase velocity under said ZnO nanotips.

43. The device of claim 41 wherein said ZnO nanotips enhance binding strength and immobilization of the targeted DNA, protein molecules or small biomolecules.

44. The device of claim 41 wherein said piezoelectric substrate is transparent and the device is operable in optical mode simultaneously with the SAW mode.

45. The device of claim 41 wherein upon illumination of UV light on said device, the change in UV absorption is detectable due to a biological and biochemical reaction of sensor layer of immobilized DNA, protein molecules on the ZnO nanotips with targeted DNA, protein molecules or small biomolecules.

46. The device of claim 41 wherein said insulating layer is replaced with a resistor-type conductive layer and the device is operable in electrical mode simultaneously with SAW mode.

47. The device of claim 46 wherein said piezoelectric substrate is replaced with a layered structure composed of a piezoelectric layer on a non-piezoelectric substrate.

48. The device of claim 47 wherein sad piezoelectric substrate is replaced with a combination of said piezoelectric layer and a non-piezoelectric layer on said non-piezoelectric substrate.

49. The device of claim 48 wherein said piezoelectric substrate is replaced with a layered structure composed of said piezoelectric layer on said piezoelectric substrate.

50. The device of claim 49 wherein said piezoelectric substrate is replaced with said non-piezoelectric layer on said piezoelectric substrate.

51. The device of claim 50, wherein said piezoelectric substrate is replaced with combination of said piezoelectric layer and said non-piezoelectric layer on said piezoelectric substrate.

52. A ZnO nanotip BAW crystal resonator sensor device, comprising:
a piezoelectric layer;
a conductive film serving as a bottom electrode deposited and patterned beneath said piezoelectric layer;
a metal electrode serving as a top electrode deposited and patterned on said piezoelectric substrate; and
ZnO nanotips deposited and patterned on the top surface of said piezoelectric layer.

53. The device of claim 52 wherein upon binding of the targeted molecules with immobilized biomolecules on said ZnO nanotips causes a mass loading on the BAW resulting in a change in the resonance frequency of the sensor device.

54. The device of claim 52 wherein said ZnO nanotips enhance binding strength and immobilization of the DNA, protein molecules or small biomolecules.

55. The device of claim 52 wherein said piezoelectric layer comprises a single crystal piezoelectric substrate.

56. The device of claim 52 wherein said piezoelectric layer comprises a piezoelectric thin film.

57. The biochip of claim 56 wherein said sensors can be operated simultaneously in conductivity mode, optical mode, SAW mode or BAW mode, and combinations thereof.

58. A ZnO nanotip biochip comprising arrays of ZnO nanotip conductivity mode biosensor devices, ZnO nanotip-gate FET biosensor devices and ZnO nanotip SAW or BAW biosensor devices, and combinations thereof.

* * * * *

UNITED STATES PATENT AND TRADEMARK OFFICE
CERTIFICATE OF CORRECTION

PATENT NO. : 6,914,279 B2
DATED : July 5, 2005
INVENTOR(S) : Lu et al.

It is certified that error appears in the above-identified patent and that said Letters Patent is hereby corrected as shown below:

Column 4,
Lines 64-65, reads "...such an FET can be a..."; should read -- ... such a FET can be a... --.

Column 6,
Line 11, reads "...This will results in a phase..."; should read -- ...This will result in a phase... --.
Line 51, reads "...electrodes, 963 $\mu$cm long..."; should read -- ...electrodes, 963 $\mu$m long... --.

Column 12,
Line 39, reads "...claim 19wherein upon..."; should read -- ...claim 19 wherein upon... --.

Column 13,
Line 57, reads "...said layer, wherein said combination..."; should read -- ...said layer, to form a combination, wherein said combination... --.
Lines 59-60, reads "...and the layer structure is engaged..."; should read -- ...and the amorphous layer is engaged ... --.

Signed and Sealed this

Fourth Day of October, 2005

JON W. DUDAS
*Director of the United States Patent and Trademark Office*